US005725886A

United States Patent [19]

Erkoboni et al.

[11] Patent Number: 5,725,886
[45] Date of Patent: Mar. 10, 1998

[54] MICROCRYSTALLINE CELLULOSE SPHERONIZATION COMPOSITION

[75] Inventors: David F. Erkoboni, Lawrenceville, N.J.; Scott A. Fiore, Westminster, Colo.; Thomas A. Wheatley, Richboro, Pa.

[73] Assignee: FMC Corporation, Philadelphia, Pa.

[21] Appl. No.: 311,800

[22] Filed: Sep. 26, 1994

Related U.S. Application Data

[63] Continuation-in-part of Ser. No. 816,027, Dec. 30, 1991.
[51] Int. Cl.⁶ .................................................. A61K 9/16
[52] U.S. Cl. .................................... 424/499; 424/500
[58] Field of Search ................................ 424/489, 494, 424/497, 499, 501; 428/402, 402.24, 403, 407; 514/951; 426/473, 516; 430/138; 502/8; 264/5, 6, 8–14, 15

[56] References Cited

U.S. PATENT DOCUMENTS

| | | | |
|---|---|---|---|
| 4,421,778 | 12/1983 | Kahn et al. | 426/564 |
| 4,837,030 | 6/1989 | Valorose, Jr. et al. | 424/456 |
| 4,867,985 | 9/1989 | Heafield et al. | 424/461 |

*Primary Examiner*—Edward J. Weberman
*Attorney, Agent, or Firm*—Robert L. Andersen; Anthony L. Cupoli

[57] ABSTRACT

A particulate co-processed unattrited microcrystalline cellulose:hydrocolloid composition wherein the respective components are present in a weight ratio of from about 99:1 to 70:30. The composition is useful as a spheronizing agent for producing spheroids of uniform size and sphericity and having high drug loadings. The composition is produced by drying a slurry of the microcrystalline cellulose in an aqueous solution of the hydrocolloid. The preferred hydrocolloid is methylcellulose.

18 Claims, No Drawings

MICROCRYSTALLINE CELLULOSE SPHERONIZATION COMPOSITION

FIELD OF THE INVENTION

This application is a continuation-in-part of U.S. Ser. No. 816,027, filed Dec. 30, 1991.

This invention relates to spheronization compositions and solid pharmaceutical dosage forms made therewith. More particularly, the invention pertains to a microcrystalline cellulose:hydrocolloid spheronizing composition capable of yielding spheronized solid dosage forms having high drug loadings.

The extrusion/spheronization method of preparing oral medications in the form of drug carrying spheroids is of growing interest to the pharmaceutical industry. Such spheroids are useful for controlled release applications.

Basically, extrusion/spheronization involves the steps of dry blending drug and excipients; wet granulation of the dry blend and extrusion of the wet mass through a screen having openings of about 0.5–2.0 mm to produce compacted cylindrical strands and spheronization of the strands in a spheronizer. The latter is essentially a device equipped with a grooved or serrated rotating disk.

Under the tumbling/roping like action of the rotating disk, the cylindrical strands are broken into smaller segments which undergo smoothing and rounding to form the spheroids which are then dried. For a more detailed description of the spheronization process, reference is made to "A New Technique for the Production of Spherical Particles" by A. D. Reynolds in Manufacturing Chemist.

In carrying out the extrusion/spheronization, it is important that the wet granulated material not adhere to the screen or feed screw of the extruder to the spheronizer; yet it must form a cohesive plastic mass while affording sufficient lubrication during extrusion through the feed chamber and screws.

A spheronizing agent exhibiting the desiderata aforesaid to a marked degree is microcrystalline cellulose, a highly purified form of cellulose consisting of crystal aggregates or crystallites as they are usually termed. However, as the ratio of drug to microcrystalline cellulose is increased and approaches 80%, processing difficulties begin to arise as well as reduced yields of spheres in the optimal size range of 0.8–1.4 mm. Also, such high drug loadings tend to diminish the mechanical strength of the spheroids thereby rendering them excessively friable. Other undesirable effects of high drug loadings are a loss of sphericity and surface smoothness. Round smooth spheroids are required for application of sustained-release coatings. High drug loadings in solid medicaments are desirable in that the physical size of the dosage form can be reduced for easier swallowing. In the case of spheroids, this means that a smaller size capsule can be used.

It has been reported that the problems associated with high drug loadings in spheroids can be reduced by adding a binder in the form of a water-soluble resin or polymer to the dry blend feed; see "Binder Effectiveness for Beads With High Drug Levels," Funck, J. A. B., Schwartz, J. B., Reilly, W. J. and Ghali, E., see DDIP 17(9), 1143–1156 (1991). U.S. Pat. No. 5,049,394 to Howard also discloses mixing a water-soluble binder with microcrystalline cellulose to produce spheroids with high drug loadings. The binder was added to minimize friability.

It is, of course, a common practice to include a hydrocolloid binder in a microcrystalline cellulose spheronizing medium for various purposes, such as altering the drug release characteristics of spheroids; see, for instance, U.S. Pat. Nos. 4,837,030 to Valerose, Jr. et al.; 4,844,910 to Leslie et al; 4,867,985 to Leslie et al. and 4,867,987 to Seth.

A known spheronizing agent capable of forming spheroids containing elevated drug levels is colloidal microcrystalline cellulose. This product is made by subjecting microcrystalline cellulose to intense mechanical attrition in an aqueous medium whereby the crystallites are broken down into submicron particles. The attrited mixture is dried in the presence of sodium carboxymethylcellulose to give water dispersible particles which form a gel when added to water. Colloidal microcrystalline cellulose and its preparation are described in U.S. Pat. No. 3,539,365 to H. W. Durand et al. It is manufactured and sold by the FMC Corporation as AVICEL$^R$ RC/CL and is listed as microcrystalline cellulose and carboxymethylcellulose sodium in the U.S. Pharmacopieia/National Formulary. Spheres made therewith are described in FMC Technical Bulletin PH-65.

Although colloidal microcrystalline cellulose/carboxymethylcellulose is an effective spheronizing agent, it tends to form a sticky granulation which clings to the processing equipment necessitating frequent disassembly and cleaning.

A microcrystalline cellulose spheronizing agent has now been found which affords surprisingly high yields of pharmaceutical grade spheroids containing elevated drug loadings and the provision of said spheronizing agent, its preparation and the said spheroids produced therewith by extrusion/spheronization constitute the principal objects and purposes of the invention. Other objects and purposes will become evident in the ensuing description.

SUMMARY OF THE INVENTION

The microcrystalline cellulose spheronizing agent of the invention consists essentially of particles of a dried homogeneous slurry of microcrystalline cellulose in an aqueous solution of a nonionic hydrocolloid, the weight ratio of the microcrystalline cellulose to hydrocolloid in the dried slurry being from about 99:1 to about 70:30.

DETAILED DESCRIPTION

Microcrystalline cellulose as used in the practice of the invention is a purified, partially depolymerized cellulose that is produced by treating alpha cellulose in the form of pulp from fibrous plant materials, with a mineral acid, particularly hydrochloric acid. The acid selectively attacks the less ordered, i.e., amorphous regions of the cellulose polymer chain, thereby exposing and freeing the crystalline sites which constitute the microcrystalline cellulose. These are separated from the reaction mixture, washed to remove degraded by-products and dried.

The resulting microcrystalline cellulose is a white, odorless, tasteless, free-flowing powder, insoluble in water, organic solvents, dilute alkalies and dilute acids. For a fuller description of the product and its manufacture as above summarized, see U.S. Pat. No. 2,978,446 to Battista et al.

Nonionic hydrocolloids suitable for the purpose of the invention can be selected from a variety of hydrophilic, physiologically compatible polymers capable of forming an aqueous solution or dispersion. These are generally known entities the description of which can be found in the periodic literature and in standard texts on polymers and resins. Illustrative examples include hydroxypropyl cellulose, hydroxypropyl methylcellulose, gelatin, water soluble cellulose acetate, polyvinylpyrrolidone, starches, sodium alginate, seed extracts such as locust bean and guar; tragacanth, arabic and karoya gums. Preferred members are hydroxypropyl cellulose, hydroxypropyl methyl cellulose and polyvinylpyrrolidone.

A hydrocolloid which has been found exceptionally effective for preparing the microcrystalline spheronization compositions of the invention is methylcellulose. Granulations containing this hydrocolloid process very cleanly in the spheronization equipment with no evidence of sticking while giving a high percentage of spheroids having excellent uniformity of size distribution and sphericity.

The term "high drug loading" is generally understood in the art to mean a substrate containing at least 80% drug. Spheroids containing 80% or more of drug are considered as having high drug loadings.

In producing the microcrystalline cellulose spheronizing agent of the invention, a slurry of microcrystalline cellulose in an aqueous solution of the nonionic hydrocolloid is first prepared. This is accomplished by adding the microcrystalline cellulose to the aqueous hydrocolloid under intense agitation such as provided by a high energy dispersator as exemplified by a Cowles mixer or comparable device.

The microcrystalline cellulose is preferably the non-dried material commonly referred to as wet cake, from a conventional acid hydrolysis of cellulose. Dried microcrystalline cellulose can be used provided the agitation is sufficient to break up the agglomerated cellulose crystallites formed during drying of the wet cake.

Mixing of the microcrystalline cellulose and aqueous hydrocolloid is continued until the hydrocolloid and cellulose crystallites become intimately associated. Normally, this takes about 10 to about 60 minutes when the microcrystalline cellulose is used in the form of wet cake.

The concentration of microcrystalline cellulose and hydrocolloid in the aqueous slurry is such that the weight ratios of these components in the dried solid will fall within the specified ranges of 99:1 to 70:30, microcrystalline cellulose:hydrocolloid. Generally speaking, total amounts by weight of slurry solids will vary from about 5% to about 30%.

Certain of the hydrocolloids may form viscous solutions or even gels in aqueous media making it difficult to produce a flowable slurry. This can usually be circumvented by employing a more dilute solution of the hydrocolloid.

After the blending is complete, the slurry is dried, preferably by spray drying. Conventional spray drying equipment and operating procedures are employed. Drying gas outlet temperature is ordinarily used to control residual moisture content of the co-processed particulate material. Moisture levels of about 0.5% to about 8.0% are satisfactory with preferred levels being about 3.0% to about 5.0%.

Spheroids are produced from the spheronizing microcrystalline cellulose compositions of the invention following known spheronization procedures, preferably extrusion/spheronization. Typically, a dry blend of the composition and drug is first prepared. Water is then added slowly, with continuous mixing until a granulation of the requisite consistency is obtained. Alternatively, the drug, if it is water soluble, can be dissolved in the water, and this solution added to the MCC:hydrocolloid particulate composition.

The wet granulation is extruded through suitably sized pierced screens and spheronized using a rotating disk having a ground surface. The spheres are then dried in a fluidized bed or conventional oven to a moisture level of about 0.5% to about 5%.

As understood in the pharmaceutical art, the term "sphere" or "spheroid" means spherical particles having a diameter in the range of about 0.1 to 2.5 mm, more preferably from 0.5 to 2 mm and most preferably from 0.8 to 1.4 mm.

When a granulation containing a drug and the coprocessed microcrystalline/nonionic hydrocolloid spheronizing agent of the invention and a comparable prior art granulation containing separately incorporated microcrystalline cellulose, nonionic hydrocolloid and drug are subjected to spheronization, a surprisingly higher percentage of pharmaceutical grade spheroids in the desired 0.8–1.4 mm size range are produced with the granulation containing the spheronizing agent of the invention; see the comparison tests given in Examples 3A, 3B and 3C.

It has also been found that granulations made with the spheronizing agent of the invention are tolerant of overwetting and are non-clinging, important features that greatly contribute to the commercial prospects of the invention.

The spheronizing agent of the invention can be used to form spheres with virtually all pharmaceutical preparations and drugs and combinations of drugs, including drugs that are water soluble or water insoluble. Typical of such drugs are the following:

Analgesics—acetaminophen, ibuprofen, ketoprofen and the like, indomethacin, naproxen, acetaminophen with codeine and acetaminophen with propoxyphene napsylate.

Antibiotics—erythromycin, cephalosporins, minocycline HCl.

Antiepileptics—phensuximide, phenytoin sodium and valproate sodium.

Antihistamines—chlorpheniramine maleate, diphenhydramine hydrochloride, triprolidine hydrochloride.

Cough and Cold Drugs—dextromethorphan hydrobromide, ephedrine sulfate, quaifenesin, phenylpropanolamine hydrochloride, promethazine hydrochloride, and pseudoephedrine hydrochloride.

Cardiovascular Drugs—captopril, chlorthiazide and hydrochlorthiazide, diltiazem, nadolol, papaverine hydrochloride, procainamide hydrochloride, propranolol hydrochloride, quinidine gluconate, quinidine sulfate.

Gastrointestinal Drugs—cimetidine, loperamide hydrochloride and ranitidine.

Respiratory Drugs—albuterol sulfate, aminophylline, theophylline.

The following examples illustrate the invention in greater detail.

EXAMPLE 1

Methylcellulose (6.3 lbs at 4% moisture) having a viscosity of 15 centipoise (Dow Chemical Co. METHOCEL$^R$ A-15LV) was hydrated with 97.9 lbs of water to form a solution containing 6% solids. The hydrocolloid was added slowly to the water with overhead stirring using a commercially available variable speed mixer. In a separate slurry tank, microcrystalline cellulose (274.7 lbs of a 41.5% wet cake) was diluted with 287.8 lbs of water. The microcrystalline cellulose was added to the water and dispersed using a high energy dispersator such as a Cowles mixer at 1500 RPM until a smooth cream-like slurry was formed. The methylcellulose solution was added to the microcrystalline cellulose with continued stirring for 40 minutes using the high energy mixer to form a uniform dispersion. The final slurry had a solids content of 18%. The slurry was then spray dried using a single fluid nozzle for atomization. The conditions were 1500 psi line pressure and a flow rate of 0.5 gpm. An outlet temperature of 230° F.–240° F. was maintained. The production rate at these conditions was 46 lbs/hr.

EXAMPLE 2

A co-processed material containing 95% microcrystalline cellulose and 5% hydroxypropylmethyl cellulose was prepared using process and conditions similar to those described in Example 1.

EXAMPLE 3

The co-processed material described in Example 1 (95/5 microcrystalline cellulose/methylcellulose—MCC/MC) was used in the preparation of spheres containing 80% theophylline using the extrusion/spheronization procedure. The co-processed 95/5 MCC/MC (200 g) along with 800 g of anhydrous theophylline was charged into a 12 quart planetary mixer and allowed to mix for a period of 5 minutes until a homogeneous mixture was achieved. To this mixture 600 g of water was added slowly with continued mixing for a period of 15 minutes allowing for sufficient distribution of the water throughout the mass. This process of wetting powders is commonly referred to as granulation. The so-obtained wet mass was then charged into the hopper of a Nica extruder. It was extruded through screens having 1.0 mm openings, at a speed of 14–16 RPM to form a pelletlike extrudate having an approximate length between 0.25 and 1.0 cm. The extrudate was then charged into the Nica spheronizer. This piece of equipment consists of a bowl having stationary side walls and a rotating bottom commonly referred to as the disk. The extrudate was processed in the spheronizer for a period of 8 minutes at a disk speed of 650 RPM. At the end of 8 minutes, the spheres were discharged into an appropriate receptacle. The spheres were then transferred onto trays of a conventional forced air oven and dried at 50° C. for a period of 6 hours. 90% of the so-obtained spheroids were within the range of 0.8 to 1.4 mm.

B. PRIOR ART SPHEROIDS

Microcrystalline cellulose (190 g), methylcellulose (10 g) and 800 g of anhydrous theophylline were dry blended and subjected to spheronization following the procedure of Example 3A. 73% of the so-obtained spheroids were within the size range of 0.8 to 1.4 mm. This Example illustrates the spheronizing procedure in which all three components aforesaid are spheronized as disclosed in the prior art see cited U.S. Pat. Nos. 4,867,985 and 4,867,987.

C. PRIOR ART SPHEROIDS

Microcrystalline cellulose 200 g and 800 g anhydrous theophylline were dry blended and subjected to spheronization following the procedure of Example 3A. 68% of the resulting spheroids were within the size range of 0.8 to 1.4 mm. This Example illustrates the spheronizing procedure in which microcrystalline is the sole spheronizing agent.

As is readily apparent from the foregoing comparative Example 3, the percent of spheroids in the desired range of 0.8 to 1.4 mm is surprisingly greater using the spheronizing agent of the invention (Example 3A) than is obtained with the prior art compositions (Examples 3B and 3C) employing the dry blends of microcrystalline cellulose:hydrocolloid and drug as separate components.

We claim:

1. A microcrystalline cellulose spheronizing agent consisting essentially of particles of a dried slurry of microcrystalline cellulose selected from the group consisting of wet cake and dried wet cake in an aqueous physiologically compatible nonionic hydrocolloid, the weight ratio of the microcrystalline cellulose to the hydrocolloid being from about 97.5:2.5 to about 70:30, and the hydrocolloid being selected from at least one of the group consisting of methylcellulose, hydroxypropyl methylcellulose, hydroxypropyl cellulose, and polyvinylpyrrolidone.

2. The spheronizing agent of claim 1 wherein the weight ratio of the microcrystalline cellulose to the hydrocolloid is from about 97.5:2.5 to about 92.5:7.5.

3. A method of producing a spheronized solid dosage form by subjecting a blend of a drug and the spheronizing agent of claim 2 to spheronization.

4. A solid dosage form comprising spheres containing, in combination, the spheronizing agent of claim 2 and a pharmaceutically effective amount of at least one drug.

5. The spheronizing agent of claim 1 wherein the weight ratio of the microcrystalline cellulose to the hydrocolloid is from about 96:4 to about 94:6.

6. A method of producing a spheronized solid dosage form by subjecting a blend of a drug and the spheronizing agent of claim 5 to spheronization.

7. A solid dosage form comprising spheres containing, in combination, the spheronizing agent of claim 5 and a pharmaceutically effective amount of at least one drug.

8. The spheronizing agent of claim 1 wherein the hydrocolloid is methylcellulose.

9. A method of producing a spheronized solid dosage form by subjecting a blend of a drug and the spheronizing agent of claim 8 to spheronization.

10. A solid dosage form comprising spheres containing, in combination, the spheronizing agent of claim 8 and a pharmaceutically effective amount of at least one drug.

11. The spheronizing agent of claim 1 wherein the microcrystalline cellulose is wet cake.

12. A method of producing a spheronized solid dosage form by subjecting a blend of a drug and the spheronizing agent of claim 11 to spheronization.

13. A solid dosage form comprising spheres containing in combination the spheronizing agent of claim 11 and a pharmaceutically effective amount of at least one drug.

14. The spheronizing agent of claim 1 wherein the hydrocolloid is hydroxypropylmethyl cellulose.

15. A method of producing a spheronized solid dosage form by subjecting a blend of a drug and the spheronizing agent of claim 14 to spheronization.

16. A solid dosage form comprising spheres containing in combination the spheronizing agent of claim 14 and a pharmaceutically effective amount of at least one drug.

17. A method of producing a spheronized solid dosage form by subjecting a blend of a drug and the spheronizing agent of claim 1 to spheronization.

18. A solid dosage form comprising spheres containing, in combination, the spheronizing agent of claim 1 and a pharmaceutically effective amount of at least one drug.

* * * * *